United States Patent [19]

Hendel et al.

[11] Patent Number: 5,436,256
[45] Date of Patent: Jul. 25, 1995

[54] PROCESS FOR THE PREPARATION OF ARYLHYDANTOINS

[75] Inventors: Wolfram Hendel, Leonding; Engelbert Kloimstein, Eferding; Klaus Fitzinger, Linz; Antonia Viehböck, Linz; Kurt Haidinger, Linz, all of Austria

[73] Assignee: Chemie Linz Gesellschaft m.b.H., Linz, Austria

[21] Appl. No.: 157,407

[22] Filed: Nov. 26, 1993

[30] Foreign Application Priority Data

Nov. 27, 1992 [AT] Austria ................................ 2355/92

[51] Int. Cl.⁶ .................. C07D 233/74; C07D 233/76; C07D 233/78
[52] U.S. Cl. .............................. 548/321.1; 548/317.1
[58] Field of Search ................. 548/316.7, 321.1, 317.1

[56] References Cited

U.S. PATENT DOCUMENTS 5,126,459 6/1992 Yamada et al. ...................... 548/314
5,196,545 3/1993 Schermanz et al. ............. 548/318.1

FOREIGN PATENT DOCUMENTS 0008547 3/1980 European Pat. Off. .
0474112 3/1992 European Pat. Off. .
2012756 8/1979 United Kingdom .
1572316 7/1980 United Kingdom .
2053206 2/1981 United Kingdom .

OTHER PUBLICATIONS

Chemical Abstracts vol. 92: col. 146767b, (1980).
Chemical Abstracts vol. 92: col. 58782x (1980).
J. Org. Chem. 9 21-30 (1944), E. K. Harvill et al.

Primary Examiner—Jacqueline Haley
Attorney, Agent, or Firm—Wenderoth, Lind & Ponack

[57] ABSTRACT

Process for the preparation of 5-arylhydantoins by reaction of an allantoin acid alkyl ester with an aryl compound in a concentrated inorganic acid at temperatures from room temperature to 150° C., with or without a phase transfer agent.

8 Claims, No Drawings

PROCESS FOR THE PREPARATION OF ARYLHYDANTOINS

Arylhydantoins are valuable intermediate products for the preparation of enantiomerically pure arylamino acids which are used, for example, in pharmacy.

Processes for the preparation of arylhydantoins have already been known for a long time. Thus, for example, according to E. K. Harvill et al., J. Org. Chem. 9, 26 (1944), 5-(4-hydroxyphenyl)hydantoin can be prepared by reaction of p-hydroxybenzaldehyde with potassium cyanide and ammonium carbonate with aqueous, alcoholic solution. However, cyanides are toxic and are employed in industrial only if unavoidable.

GB-A-2 012 756 discloses that 5-arylhydantoins can be obtained by reaction of urea with an alpha-aryl-alpha-hydroxy acetic acid. The alpha-aryl-alpha-hydroxy acid is prepared by reaction of glyoxylic acid with an aryl compound in an aqueous medium in the presence of an alkali metal hydroxide, but isomer mixtures which are difficult to separate are formed, so that this reaction in general only achieves low yields.

GB-A-2 053 206 discloses the preparation of 5-arylhydantoins by reaction of allantoin with an aryl derivative in a hot, acid medium. However, allantoin must first be prepared for the reaction.

According to GB-A-1 572 316, 5-(4-hydroxyphenyl)-hydantoin can be prepared from simple starting compounds that is to say from glyoxylic acid, urea and phenol, in aqueous, acidic solution. However, it has been found that the product of this reaction is rather contaminated by its isomer 5-(2-hydroxyphenyl)hydantoin, which can be separated off only with difficulty.

According to EP-A-0 474 112, glyoxylic acid methyl ester methyl hemiacetal is reacted with urea and an aryl compound in a one-pot process for preparation of 5-arylhydantoins with a good purity.

However, the long reaction times of 20 hours or more are unacceptable for an industrial process.

Unexpectedly, it has now been found that 5-arylhydantoins are obtained in a high purity in a 2-stage reaction starting from simple, non-toxic starting compounds if, in a 1st reaction stage, a glyoxylic acid alkyl ester alkyl hemiacetal is reacted with urea to give allantoin acid alkyl ester, which is isolated and, in a 2nd reaction stage allowed to react with an aryl compound, whereby the reaction times in both cases are unexpectedly short.

The invention therefore relates to a process for the preparation of 5-arylhydantoins of the general formula

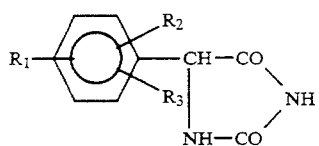

in which $R_1$, $R_2$ and $R_3$ independently of one another denote hydrogen, an alkyl- or an alkoxy group each having from 1 to 6 C-atoms, a hydroxyl- or a halogen group, or an amino group which is substituted by an aryl group having 1 to 8 C-atoms, by an alkyl group having 1 to 6 C-atoms or by a phenyl group, which comprises reacting an allantoin acid alkyl ester of the general formula

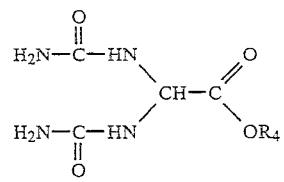

in which $R_4$ denotes an alkyl group having 1 to 8 C atoms, in a concentrated, inorganic acid at temperatures from room temperature to 150° C., with or without a phase transfer agent, with an aryl compound of the general formula

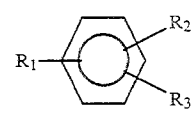

in which $R_1$, $R_2$ and $R_3$ have the abovementioned meaning.

In the general formula I, $R_1$, $R_2$ and $R_3$ independently of one another denote hydrogen, an alkyl, alkoxy, hydroxyl or halogen group or an amino group which is substituted by groups which are inert under the reaction conditions. Alkyl or alkoxy groups are to be understood as groups having 1 to 6, preferably 1 to 3, C atoms, for example methyl, ethyl, propyl, iso-propyl or hexyl chlorine or bromine. Amino groups which are protected by groups which are inert under the reaction conditions are amino groups which are substituted by acyl groups having 1 to 8 C atoms, preferably by the acetyl group, by alkyl groups having 1 to 6 C atoms or by phenyl groups. Preferably, $R_1$, $R_2$ and $R_3$ independently of one another denote hydrogen or hydroxyl, alkoxy, halogen or substituted amino groups. Especially preferably, $R_1$ denotes hydrogen and $R_2$ and $R_3$ independently of one another denote hydrogen, hydroxyl or alkoxy groups or amino groups which are substituted by alkyl groups.

In the general formula II, $R_4$ denotes an alkyl group having 1 to 8 C atoms. An alkyl group here is to be understood as a straight-chain or branched alkyl group, for example a methyl, ethyl, propyl, iso-propyl iso-pentyl, hexyl or octyl group, preferably a methyl, ethyl, iso-propyl, butyl or hexyl group. The preparation of compounds of the formula II can be carried out by reaction of a glyoxylic acid alkyl ester alkyl hemiacetal with urea in the presence of an alkyl alcohol and a mineral acid. The preparation of the allantoin acid methyl ester from glyoxylic acid methyl ester methyl hemiacetal and urea in the presence of an inorganic acid and methanol is disclosed, for example, in U.S. Pat. No. 5,196,545. This reaction is in general concluded within a few hours.

In the general formula III, $R_1$, $R_2$ and $R_3$ have the meaning given in the general formula I. Especially preferred compounds of the general formula III are benzene, phenol, dihydroxybenzene, anisole, guaiacol, veratrol and trimethoxybenzene.

For carrying out the reaction according to the invention, the compound of the formula II and the compound of the formula III are initially introduced into an inorganic acid. In general, 1 to 6, preferably 1 to 3 mol of the compound of the formula III are employed per mol of the compound of the formula II. However, it may be advantageous in individual cases to employ the compound of the formula III in less than the molar amount.

Mineral acids such as hydrochloric acid, sulfuric acid or mixtures of such acids are employed as the inorganic acids. The amount of acid depends on the nature of compound III, which in some cases is only sparingly soluble in the acid. To increase the solubility of the compound III in the acid, a phase transfer agent, for example, a liquid, organic acid, such as acetic acid or propionic acid, preferably acetic acid, is employed if appropriate.

The reaction mixture is stirred at temperatures from about room temperature to 150° C., preferably at temperatures of from 60° to 120° C., particularly preferably of from 70° to 100° C. If appropriate, the reaction is carried out under pressure, customary pressures of up to 0.3 to 2 MPa being applied.

The 5-arylhydantoin of the formula I is formed thereby. The course of the reaction can be monitored with the aid of customary methods, for example gas chromatography or thin layer chromatography. The reaction proceeds in an unexpectedly short time, and in some cases has ended after only 2 hours. The position, in the aryl ring of the formula III in which the allantoin acid alkyl ester of the formula II reacts depends on the nature of the substituents $R_1$, $R_2$ and $R_3$ and their particular position in the aryl ring of the formula III. As is known, the nature of a substituent in an aryl ring affects the charge density distribution in the molecule, and the position of a substituent in the aryl ring further affects, depending on the intensity of the inductive or mesomeric effect, that position in which another substituent is introduced by a reaction. In the case of substituents in the aryl ring which are not hydrogen, the position of the reaction center in the aryl ring depends on the intensity of the particular inductive or mesomeric effect of the individual substituents. It has been found that in the case where $R_1$ in formula III denotes a hydroxyl group and $R_2$ and $R_3$ denote hydrogen, the reaction proceeds mainly in the para-position. In individual cases where the position of the reaction center cannot be predicted with certainty, one preliminary experiment by which the product prepared can be characterized is sufficient.

After the reaction has ended, the reaction mixture is cooled. The 5-arylhydantoin can crystallize and can be isolated by customary methods, such as filtration or centrifugation. It has been found, unexpectedly, that 5-(4-hydroxyphenyl)hydantoin prepared according to the invention crystallizes out in relatively large crystals and is therefore particularly easily and readily filterable, the 5-(4-hydroxyphenyl)hydantoin which was obtained by the preparation processes known to date in general being very finely crystalline, so that difficulties occurred during solid/liquid separation.

If the 5-arylhydantoin does not crystallize the reaction mixture can be extracted with the aid of suitable organic, solvents, after neutralization and if appropriate after evaporative concentration, and the 5-arylhydantoin can be isolated in this manner. Neutralization means adjusting the pH to a value at which the 5-arylhydantoin formed does not yet form a salt. A pH of 3 to 9 is usually established. Suitable organic solvents are, for example, carboxylic acid esters, for example ethyl or butyl acetate, ethers, for example methyl tert-butyl ether, diisopropyl ether or tetrahydrofuran, ketones, for example acetone, methyl ethyl ketone or diisobutyl ketone, alcohols which are water-immiscible or chlorinated hydrocarbons, such as methylene chloride or trichloroethylene. Carboxylic acid esters, ethers or ketones are preferred, and carboxylic acid esters are particularly preferred.

It has been found that the purity of the 5-(4-hydroxyphenyl)hydantoin isolated in the manner described is in general more than 99%, and is therefore sufficient. For special cases, the purity of the 5-(4-hydroxyphenyl)hydantoin can be increased further by heating in water to the reflux temperature. In other cases, purification by extractive or chromatographic methods or by recrystallization can follow.

In a preferred embodiment of the invention, about 2 to 3 mol of a compound of the formula III in which $R_1$, $R_2$ and $R_3$ independently of one another denote hydrogen, hydroxyl, alkoxy groups or amino groups which are substituted by alkyl groups per mol of a compound of the general formula II in which $R_4$ denotes an alkyl group having 1 to 6 C atoms are initially introduced into the reaction vessel in concentrated hydrochloric acid or sulfuric acid and the mixture is heated to temperatures of from 70° to 100° C., while stirring. After the reaction has ended, the reaction mixture is cooled. If the product is obtained in crystalline form, it is filtered off, and the product which has been filtered off is heated in water to the reflux temperature, if appropriate, cooled and filtered.

If the product is not obtained in crystalline form, the reaction mixture is either brought to a pH of between 3 and 9 by addition of sodium hydroxide solution and concentrated by evaporation and the residue is extracted with a carboxylic acid ester, or water is added to the reaction mixture and the aqueous mixture is extracted with an organic, water-immiscible solvent, if appropriate after adjusting the pH to pH 3 to 9 by addition of sodium hydroxide solution. The organic solvent is evaporated off, if appropriate after drying, and if appropriate the residue is purified further by customary methods, such as recrystallization or chromatography.

Allantoin acid methyl ester which has been prepared by reaction of glyoxylic acid methyl ester methyl hemiacetal and urea in methanol in the presence of sulfuric acid is preferably employed in the process. The invention likewise relates to the preparation of a 5-arylhydantoin of the general formula I starting from a glyoxylic acid alkyl ester alkyl hemiacetal and urea, which are reacted in a first stage according to the manner disclosed in U.S. Pat. No. 5,196,545 to give the allantoin acid alkyl ester of the general formula II, isolation of the allantoin acid alkyl ester of the general formula II and reaction of the allantoin acid alkyl ester isolated with an aryl compound of the general formula III in a concentrated, inorganic acid at temperatures from room temperature to 150° C. with or without a phase transfer agent.

5-Arylhydantoins are prepared in short reaction times and in a good purity and satisfactory yield in the manner described. The process therefore represents an enrichment of the art.

EXAMPLE 1

A) A mixture of 240 g of glyoxylic acid methyl ester methyl hemiacetal (2.0 mol), 400 g of urea (6.66 mol), 240 g of methanol and 100 g of 8% strength methanolic sulfuric acid was heated under reflux for 5 hours, while stirring. Thereafter, the reaction had ended and the reaction mixture was cooled to room temperature, whereupon a colorless precipitate separated out, which was filtered off and, after washing with methanol, was dried at 70° C. in vacuo.

334.1 g, that is to say 88% of theory, of allantoin acid methyl ester were obtained by this reaction.

$^1$H-NMR (DMSO): δ=3.63 (s, 3H, COOCH$_3$), 5.32 (t, 1H, J=8 Hz, CH) 5.82 (s, 4H, NH$_2$), 6.92 (d, 2H, J=8 Hz, NH)

B) 125.1 g of allantoin acid methyl ester (0.66 mol), 187.5 g of phenol (1.99 mol) and 225 ml of 36% strength HCl were heated at 83° C. for 4 hours. From the initially clear, colorless solution, a precipitate started to crystallize after about 15 to 20 minutes. After the reaction had ended, the reaction mixture was cooled to 15° C. and stirred for a further 2 hours. The precipitate was filtered off, washed with warm water and suspended in moist state in 375 ml of water, and the suspension was stirred under reflux for 2 hours. After cooling, filtration and washing with water, the precipitate was dried at 80° C. in vacuo.

79.7 g, that is to say 63% of theory, of D,L-5-(4-hydroxyphenyl)hydantoin with a purity of 99.4% and a melting point of 267° C. were obtained by this reaction.

$^1$H-NMR (DMSO): δ=5.06 (s, 1H, CH), 6.83 (d, 2H, J=8.4 Hz, Ar) 7.16 (d, 2H, J=8.4 Hz, Ar), 8.33 (s, 1H, NH), 9.6-10.6 (s br, NH)

The content of isomeric 5-(2-hydroxyphenyl)hydantoin was 0.2%. The yield over the two reaction stages A) and B) was 55% of theory, based on glyoxylic acid methyl ester methyl hemiacetal.

The isomer purity of the compound prepared was determined with the aid of high pressure liquid chromatography:

Data system: Hewlett-Packard Chemstation
Column: Phenyl Bondapak 10 μm, Waters
Temperature: room temperature
Mobile phase: water-acetonitrile 88:12
Flow rate: 0.6 ml/minute
Detector: UV, 254 nm Under these conditions, the retention times were about 9 minutes for 5-(4-hydroxyphenyl)hydantoin and about 11 minutes for the isomeric 5-(2-hydroxyphenyl)-hydantoin.

EXAMPLE 2

A mixture of 23.8 g of allantoin acid methyl ester (125 mmol), 50 g of benzene (0.64 mol) and 50 g of concentrated sulfuric acid was heated at 80° C. for 2 hours. The reaction had then ended. The reaction mixture was cooled to room temperature, brought to pH 4 with 50% strength sodium hydroxide solution and extracted with ethyl acetate, and the organic phase was dried and evaporated. The residue was recrystallized from water.

10.5 g, that is to say 47.7% of theory, of D,L-5-phenylhydantoin with a melting point of 151° C. were obtained by this reaction.

$^1$H-NMR (DMSO): δ=5.21 (s, 1H, CH), 7.35-7.50 (m, 5H, Ar), 8.46 (s, 1H, NH), 10.6-11.2 (s br, NH)

EXAMPLE 3

A mixture of 83.4 g of allantoin acid methyl ester (0.44 mol), 146.45 g of pyrocatechol (1.33 mol) and 250 ml of 36% strength HCl was heated at 80° C. for 2.5 hours, while stirring vigorously. The reaction had then ended. The clear solution was cooled, no crystallization occurring. The reaction solution was brought to pH 4.4 by addition of 50% strength sodium hydroxide solution and evaporated, the residue which remained was extracted exhaustively with ethyl acetate in a Soxhlet extractor, the ethyl acetate phase was concentrated and the product was crystallized.

61.8 g, that is to say 67% of theory, of D,L-5-(3,4-dihydroxyphenyl)hydantoin with a melting point of 231° to 233° C. were obtained by this reaction.

EXAMPLE 4

50 g of concentrated sulfuric acid were added to a mixture of 23.8 g of allantoin acid methyl ester (0.125 mol), 36.4 g of N,N-dimethylaniline (0.3 mol) and 12.5 g of acetic acid in the course of 30 minutes, the reaction mixture heating up to 90° C. The reaction mixture was heated at 90° to 95° C. for 5 hours, after which the reaction had ended. After the reaction mixture had been cooled, the pH was brought to pH 8 with the aid of 90 ml of 30% strength NaOH, after which water and excess N,N-dimethylaniline were distilled off in vacuo. The residue was extracted exhaustively in a Soxhlet extractor, first with ethyl acetate and then with methyl isobutyl ketone. The material obtained from the methyl isobutyl ketone extract was purified by column chromatography (silica gel, chloroform:methanol=49:1). After digestion of the product in acetone and hexane and recrystallization from methyl isobutyl ketone, D,L-5-(4-dimethylaminophenyl)hydantoin was obtained in the form of red crystals with a melting point of 228° to 230° C.

$^1$H-NMR (DMSO): δ=2.92 (s, 6H, N—CH$_3$), 5.02 (s, 1H, CH), 6.76 (d, 2H, J=8.5 Hz, Ar), 7.15 (d, 2H, J=8.5 Hz, Ar), 8.28 (s, 1H, NH), 10.4-11.0 (s br, NH)

EXAMPLE 5

50.0 g of concentrated H$_2$SO$_4$ were added to a mixture of 23.8 g of allantoin acid methyl ester (0.125 mol) and 50.0 g of 1,2,3-trimethoxybenzene (0.297 mol) while stirring vigorously, during which the mixture heated up to 40° C. The reaction mixture was heated at 95° to 98° C. for 5 hours and, after cooling, brought to pH 8 with 30% strength NaOH. Excess trimethoxybenzene was extracted with the aid of hexane. The aqueous phase was evaporated in vacuo and the residue which remained was extracted exhaustively with acetone. The material isolated from the acetone extract was filtered over silica gel and purified by column chromatography (silica gel, chloroform:methanol= 49:1). After digestion of the product in acetone and hexane and recrystallization from methyl isobutyl ketone D,L-5-(3,4,5-trimethoxyphenyl)hydantoin was obtained in the form of colorless crystals with a melting point of 153.3° to 154.4° C.

$^1$H-NMR (DMSO): δ=3.79 (s, 3H, OCH3), 3.82 (s, 3H, OCH3), 3.84 (s, J=3 Hz, OCH3), 5.11 (s, 1H, CH), 6.84 (d, 2H, J=8.6 Hz, Ar), 6.99 (d, 2H, J=8.6 Hz, Ar), 8.10 (s, 1H, NH), 10.4-11.0 (s br, NH)

EXAMPLE 6

A) A mixture of 22.2 g of glyoxylic acid ethyl ester ethyl hemiacetal (0.15 mol), 30.0 g of urea (0.5 mol), 90 g of ethanol and 7.5 g of 8% strength ethanolic sulfuric acid was heated under reflux for 4 hours. Thereafter, the reaction had ended and the reaction mixture was cooled to room temperature, whereupon a colorless precipitate separated out, which was filtered off, washed three times with ethanol and dried in vacuo at 70° C. 24.5 g, that is to say 80% of theory, of allantoin acid ethyl ester were obtained by this reaction.

$^1$H-NMR (DMSO): δ=1.19 (t, 3H, J=7 Hz, COOCH$_2$CH$_3$), 4.10 (q, 2H, J=7 Hz, COOCH$_3$CH$_3$), 5.29 (t, 1H, J=8 Hz, CH), 5.85 (s, 4H, NH₂), 6.94 (d, 2H, J=8 Hz, NH)

B) 23.0 g of allantoin acid ethyl ester (0.11 mol), 31.2 g of phenol (0.33 mol) and 37.5 ml of 36% strength HCl were heated at 84° C. for 4 hours. From the initially clear, colorless solution, a precipitate started to crystallize after about 15 to 20 minutes. After the reaction has ended, the reaction mixture was cooled to 15° C. in the course of one hour and stirred for a further 2 hours. The precipitate was filtered off, washed twice each with 75 ml of water of 60° C. and suspended in the moist state in 63 ml of water, and the suspension was stirred under reflux for 2 hours. After cooling, filtration, washing with water and drying, 13.6 g, that is to say 57% of theory, of D,L-5-(4-hydroxyphenyl)hydantoin were obtained with a purity of 99.3% and a melting point of 267° C. The content of isomeric 5-(2-hydroxyphenyl)hydantoin was less than 0.1%.

The yield over the two reaction stages A) and B) was 46% of theory, based on the glyoxylic acid ethyl ester ethyl hemiacetal.

EXAMPLE 7

A) A mixture of 26.4 g of glyoxylic acid propyl ester propyl hemiacetal (0.15 mol), 30.0 g of urea (0.5 mol), 600 g of propanol and 7.5 g of 8% strength propanolic sulfuric acid was heated under reflux for 4 hours. Thereafter, the reaction had ended and the reaction mixture was cooled to room temperature, whereupon a colorless precipitate separated out, which was filtered off, washed with methanol and dried in vacuo at 50° C. 13.6 g, that is to say 42% of theory, of crystalline allantoin acid propyl ester were obtained by this reaction.

¹H-NMR (DMSO): δ=0.91 (t, 3H, J=7.3 Hz, CH₂—CH₂—CH₃), 1.90 (m, 2H, CH₂—CH₂CH₃), 4.02 (t, 2H, J=6.4 Hz, O—CH₂—CH₂—CH₃), 5.31 (t, 1H, J=8 Hz, CH), 5.81 (s, 4H, NH₂), 6.90 (d, 2H, J=8 Hz, NH)

B) 12.0 g of allantoin acid propyl ester (0.06 mol), 15.6 g of phenol (0.17 mol) and 18.8 ml of 36% strength HCl were heated at 85° to 90° C. From the initially clear, colorless solution, a precipitate started to separate out after about 5 minutes. The reaction had ended after 4 hours. The reaction mixture was cooled to 15° C. and stirred for a further 2 hours. The precipitate was filtered off, washed twice each with 75 ml of water of 60° C. and suspended in the moist state in 32 ml of water, and the suspension was stirred under reflux for 2 hours. After cooling, filtration and washing with water, the precipitate was dried in vacuo at 70° C. 5.1 g, that is to say 44% of theory, of D,L-5-(4-hydroxyphenyl)hydantoin with a melting point of 267° C. and a purity of more than 97% were obtained by this reaction. The content of isomeric D,L-5-(2-hydroxyphenyl)hydantoin was about 0.2%.

EXAMPLE 8

A) A mixture of 30.6 g of glyoxylic acid butyl ester butyl hemiacetal (0.15 mol), 30.0 g of urea (0.5 mol), 300 g of n-butanol and 7.5 g of 8% strength butanolic sulfuric acid was heated at 85° C. for a total of 4 hours. After the reaction had ended, the suspension formed was cooled to room temperature, whereupon a colorless precipitate separated out, which was filtered off, washed with methanol and dried in vacuo at 75° C. 23.1 g, that is to say 66% of theory, of crystalline allantoin acid butyl ester were obtained by this reaction.

¹H-NMR (DMSO): δ=0.89 (t, 3H, J=7.3 Hz, CH₂—CH₂—CH₂—CH₃), 1.34 (m, CH₂—CH₂—CH₂CH₃), 1.54 (m, 2H, CH₂—CH₂—CH₂—CH₃), 4.05 (t, 2H, J=6.4 Hz, O—CH₂—CH₂—CH₂—CH₃)

B) 25.5 g of allantoin acid butyl ester (0.12 mol), 31.2 g of phenol (0.33 mol) and 37.5 ml of 36% strength HCl were heated at 85° to 90° C. From the initially clear, colorless solution, a precipitate started to crystallize out after about 45 minutes. The reaction had ended after 4 hours. The reaction mixture was cooled to 15° C. and the precipitate was filtered off, washed with hot water and suspended in the moist state in 63 ml of water. The suspension was heated under reflux for 2 hours, the suspension formed was cooled to 30° C. and filtered and the residue was rinsed with cold water and dried at 70° C. in vacuo. 14.6 g, that is to say 53% of theory, of D,L-5-(4-hydroxyphenyl)hydantoin with a purity of amost 99% were obtained by this reaction. The content of isomeric 5-(2-hydroxyphenyl)hydantoin was about 0.2%.

What we claim is:

1. Process for the preparation of 5-arylhydantoins of the formula

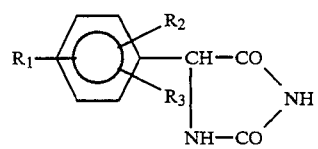

in which R₁, R₂ and R₃ independently of one another denote hydrogen, an alkyl or alkoxy group each having from 1 to 6 C atoms, a hydroxyl or a halogen group, or an amino group which is substituted by an acyl group having 1 to 8 C atoms, by an alkyl group having 1 to 6 C atoms or by a phenyl group, which comprises reacting an allantoin acid alkyl ester of the formula

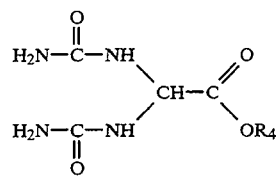

in which R₄ denotes an alkyl group having 1 to 8 C atoms, in a concentrated, inorganic acid at temperatures from room temperature to 150° C., with or without a phase transfer agent, with an aryl compound of the formula

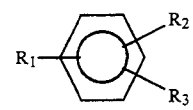

in which R₁, R₂ and R₃ have the above-mentioned meaning.

2. Process according to claim 1, wherein the allantoin acid alkyl ester of formula II is prepared by reacting a glyoxylic acid ester alkyl hemiacetal of the formula

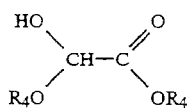

with urea in an alcohol of the formula R₄OH, in the presence of catalytic amounts of an inorganic acid.

3. Process according to claim 1, wherein in the compound of formula II, $R_4$ denotes an alkyl group having 1 to 6 C atoms.

4. Process according to claim 1, wherein in the compound of formula II or of formula IV, $R_4$ denotes an alkyl group having 1 to 6 C atoms.

5. Process according to claim 1, comprising employing hydrochloric acid or sulfuric acid as the inorganic acid.

6. Process according to claim 1, comprising carrying out the reaction of a compound of formula II with a compound of formula III at temperatures of from 60° to 120° C.

7. Process according to claim 1, comprising employing a phenol which is substituted by one or more hydroxyl or alkoxy groups or amino groups which are substituted by alkyl groups as the aryl compound of formula III.

8. Process according to claim 1, comprising employing acetic acid as the phase transfer agent.

* * * * *